United States Patent [19]
Tu et al.

[11] Patent Number: 6,104,952
[45] Date of Patent: Aug. 15, 2000

[54] DEVICES FOR TREATING CANKER SORES, TISSUES AND METHODS THEREOF

[76] Inventors: Lily Chen Tu; Hosheng Tu, both of 2151 Palermo, Tustin, Calif. 92782

[21] Appl. No.: 09/272,971

[22] Filed: Mar. 20, 1999

Related U.S. Application Data

[63] Continuation-in-part of application No. 09/004,110, Jan. 7, 1998, Pat. No. 5,968,005.
[51] Int. Cl.$^7$ ...................................................... A61N 1/30
[52] U.S. Cl. ............................................ 604/20; 607/102
[58] Field of Search .................... 604/20–22; 606/41–42, 606/45–50; 607/100–102

[56] References Cited

U.S. PATENT DOCUMENTS

| | | |
|---|---|---|
| 5,456,662 | 10/1995 | Edwards et al. . |
| 5,676,648 | 10/1997 | Henley . |
| 5,938,658 | 8/1999 | Tu . |

*Primary Examiner*—Wynn Wood Coggins
*Assistant Examiner*—LoAn H. Thanh

[57] ABSTRACT

A medical device for treating canker sores, wherein flexible RF electrode means having a distal surface plate permeable to medicament comprises therapeutic agent delivery means, is inserted into the mouth of a patient; the electrode means being placed against and/or surrounding the canker sore region; RF energy is applied for a predetermined time and temperature to the canker sore tissue through the electrode means to cause internal lesions; and delivering a heated therapeutic agent to heal the tissues thereafter for a predetermined duration.

20 Claims, 7 Drawing Sheets

FIG. 3   SECTION A-A

FIG. 5 SECTION B-B

Double Solid line: RF circuit
Dashed line: monitoring routes

DEVICES FOR TREATING CANKER SORES, TISSUES AND METHODS THEREOF

RELATIONSHIP TO COPENDING APPLICATION

This application is a continuation-in-part of application Ser. No. 09/004,110, filed on Jan. 7, 1998, which issued as U.S. Pat. No. 5,968,005 on Oct. 19, 1999, the entire contents of which are incorporated herein by reference.

TECHNICAL FIELD

The present invention generally relates to an improved medical device system and means for treating tissues. More particularly, the present invention relates to such devices and methods for treating the cold sores, canker sores, warts, fever blisters lesions, and aptheous ulcerations in a patient by delivering heated therapeutic agents to the lesion sites with controlled duration and temperature.

BACKGROUND OF THE INVENTION

Surgical procedures are usually used for the treatment of cellular tissues requiring direct contact of the target tissue with a medical instrument. Surgical procedures often lead to substantial trauma by exposing both the target and the intervening tissues. Furthermore, precise placement of a treating probe is difficult because of the location of the target tissue in the body, or the proximity of the target tissue to easily damage critical body organs, nerves, or other components.

Destruction of cellular tissues in situ has been used in the treatment of many diseases and medical conditions alone or as an adjunct to surgical removal procedures. It is often less traumatic than surgical procedures and may be the only alternative, wherein other procedures are unsafe. Ablative treatment devices have an advantage of using a destructive energy that is rapidly dissipated and reduced to a non-destructive level by conduction and convection, to forces of circulating fluids and/or other natural processes.

Devices using microwave energy, radiofrequency energy, ultrasonic energy, cryogenic, laser energy, and tissue destructive substances have been used to destroy malignant, benign, and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula that is used to carry a radiofrequency electrode, a microwave energy antenna or an ultrasonic transducer through a duct to the zone of treatment and applying energy diffusely through the duct wall into the surrounding tissue in the targeted directions.

Canker sores are also known as aphthous ulcerations or recurrent aphthae, which are painful sores usually formed in the mucous membrane of the mouth. The sores first appear as small red lesions that quickly whiten and then break down to form shallow ulcers. Many people, especially small children with less immunity to ulcerations, experience the pain and discomfort of canker sores for a period from several days up to a couple of weeks. While the cause of canker sores has not been identified, several pharmaceutical approaches have been taken. However, they only coat the surface of the canker sores by a relieving agent and mask the problem for temporary relief of pain and stress.

Price, Jr. in U.S. Pat No. 5,686,095 entitled "Method of treating canker sores" teaches a method by which a fluoroquinolone is topically applied to the ulcerous area. Similarly, Alliger in U.S. Pat. No. 5,516,799 entitled "Method of treating small mouth ulcers" teaches a method of using a simple alpha hydroxy organic acid. Marcus et al. in U.S. Pat. No. 5,182,104 entitled "Topical virucidal composition for treatment of mucocutaneous tissue" teaches a method of topically applying composition with a virucidal impact on mucocutaneous tissue, inactivation of herpes virus and human papilloma virus as manifested in cold sores, canker sores, warts, fever blisters lesions, and aptheous ulcerations. Leeds in U.S. Pat. No. 4,466,956 entitled "Method of therapy for oral herpes simplex" discloses serial application of povidone-iodine and then application of anti-inflammatory agent. Hodosh in U.S. Pat. No. 4,191,750 entitled "Method for treating canker sores" discloses a method of applying a nitrate of potassium, lithium, sodium, magnesium, calcium or strontium. However, all the above-mentioned topical treatments are not effective because the therapeutic agent is easily swept away in the mouth of a patient. None of above-mentioned patents discloses the method for treating canker sores cold sores, warts, fever blisters lesions, and aptheous ulcerations by heating the therapeutic fluid and forcing the heated fluid to contact and diffuse into the sores for a prolonged period treatment.

Of particular interest to the present invention are RF therapeutic protocols which have been proven to be highly effective as used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after locating the sore sites for treatment. Radiofrequency energy, when coupled with a temperature control mechanism, can supply precise energy to the device-to-tissue contact site to obtain the desired temperature for treating the tissue. It can also be used to heat the therapeutic fluid for therapeutically treating the canker sores for the optimal effect.

Imran in U.S. Pat. No. 5,281,218 entitled "Catheter having needle electrode for radiofrequency ablation" teaches a method using a needle electrode that is attached onto a catheter for radiofrequency ablation. Though a needle-like electrode is beneficial to ablate a tissue point for deep lesion, it is not disclosed that said needle electrode could possibly hold the heated therapeutic fluid for prolonged contact with the target tissue.

Edwards et al. in U.S. Pat. No. 5,456,662 entitled "Method for reducing snoring by RF ablation of the uvula" teaches a medical ablation method for reducing snoring wherein a flexible RF electrode wire is inserted into the uvula and RF energy is applied to the uvula tissue to cause internal lesions. Edwards et al. does not disclose a catheter to ablate an area, having capability for simultaneously delivering radiofrequency energy and a therapeutic agent.

Henley in U.S. Pat. No. 5,676,648 and 5,160,316 discloses a portable iontophoresis apparatus for facilitating delivery of medication across the cutaneous membrane into adjacent underlying tissues and blood vessels. When current flows across a patient's skin to the application electrode in response to an applied voltage, the current promotes and hastens the penetration of the medicament. Brant et al. in U.S. Pat. No. 3,163,166 discloses an iontophoresis apparatus comprising passing an electric current between a selected area of soft tissue surface and an external electrode. Preferably the electrolyte in the delivery drug comprises a thickened aqueous solution of an ionizable medicament. Powers et al. in U.S. Pat. No. 4,702,732 discloses an electrode assembly using alternating and direct electrical energy for transdermal delivery of pharmacologically active ligands and for stimulation of tissue in vivo. Glikfeld et al. in U.S. Pat. No. 5,279,543 discloses a device for iontophoretic non-invasive delivery of drugs comprising a pair of electrodes and electrical insulation between the pair of electrodes. However, the above-referred patents neither teach means for supplying a therapeutic drug to the tissue having a positive pressure for deep drug penetration, nor teach means for applying energy to heat the therapeutic drug for enhanced drug penetration and tissue treatment. Furthermore, the tissue contact electrode means should have a contact surface that is permeable to medicament so that drug can be evenly and diffusely applied to the target tissue sites or region.

While a radiofrequency procedure using an existing electrode device has had promising results, the device is exposed to the target tissue without prolonged therapeutic treatment by the therapeutic agent, resulting in inefficient treatment of canker sores. Therefore, there is a need for an improved device system and methods using the controllable radiofrequency energy for generating the needed heat to treat the sores and also to heat the therapeutic fluid. During RF energy delivery, the therapeutic agent, such as an anti-inflammatory agent or virucidal drug, is delivered to the sore sites. By having a device with temperature control means and substance delivery capability, the cold sores, canker sores, warts, fever blisters lesions, aptheous ulcerations, and the like can be treated therapeutically.

SUMMARY OF THE INVENTION

In general, it is an object of the present invention to provide a method and an improved medical device for generating and controlling heat to treat the canker sores in the mucous membrane of the mouth. It is another object of the present invention to provide a device system so that a therapeutic agent can be supplied to the canker sore sites for prolonged contact. It is another object of the present invention to provide a method and a device for monitoring the temperature of the device and controlling the temperature through a closed-loop temperature control mechanism and/ or algorithm enclosed in the RF generator. The location of the temperature sensor is preferably at the proximity of the tip portion of the medical device, more preferably at the tissue contact site. It is still another object of this invention to provide a method and a device for treating the canker sores in a patient by delivering a therapeutic agent to the lesion sites under positive pressure, controlled time, and suitable elevated temperature. It is a further object of the present invention to have the tissue-contact portion of the medical device comprising a contact surface plate that is permeable to medicament so that drug can be evenly and diffusely applied to the target tissue sites or region. The tissue to be treated in this invention is not limited to canker sores; it may include cold sores, canker sores, warts, fever blisters lesions, aptheous ulcerations, and the like as manifested by herpes virus, human papilloma virus and the like.

Briefly, heat is generated by applying a suitable energy source to a device, which comprises an electrode means, in contact with the body tissue. A suitable energy source may consist of radiofrequency energy, microwave energy, ultrasonic energy, alternating current energy, or laser energy. The energy can be applied to either the canker sores through the electrode means, or to the therapeutic agent to activate its effectiveness at a higher temperature. A DIP (dispersive indifferent pad) type pad that contacts the patient is connected to the Indifferent Electrode Connector on the RF generator as the reference electrode. When using an alternating current outlet, the generator should be grounded to avoid electrical interference. In the case of RF energy, heat is controlled by the power of the RF energy delivered and by the delivery duration. The standard RF energy generator means and its applications through the electrode means to a patient are well known for those who are skilled in the art.

In one embodiment, the device is leak-proof or watertight so that the therapeutic agent, in either fluid phase or gel phase, can be forced under a positive pressure to flow inside the lumen of said device from its proximal end to the distal end. The electrode means at the distal end of the device comprises a rim electrode, whereas the distal section of the device is bell-shaped or trumpet-shaped. The rim electrode may further comprise a tissue-contact surface plate that is permeable to medicament so that drug can be evenly and diffusely applied to the target tissue sites or region. The rim electrode and the permeable tissue-contact surface plate are collectively called as the "rim electrode means" in this invention. The tissue-contact surface plate portion of the rim electrode of the present invention may have numerous tiny throughput holes or interconnected open micropores in the range of a few microns to several thousand microns for fluid/gel permeation.

The method and apparatus of the present invention have several significant advantages over other known systems or techniques to treat the canker sores and the like. In particular, the device system comprising the rim electrode means using controllable RF energy as a heat source in this invention and simultaneously delivering therapeutic agent to the lesion sites, wherein the tissue-contact surface plate portion of the electrode means of the present invention is permeable to therapeutic medicament, results in a more efficient therapeutic effect, which is highly desirable in its intended application on canker sores and the like.

BRIEF DESCRIPTION OF THE DRAWINGS

Additional objectives and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
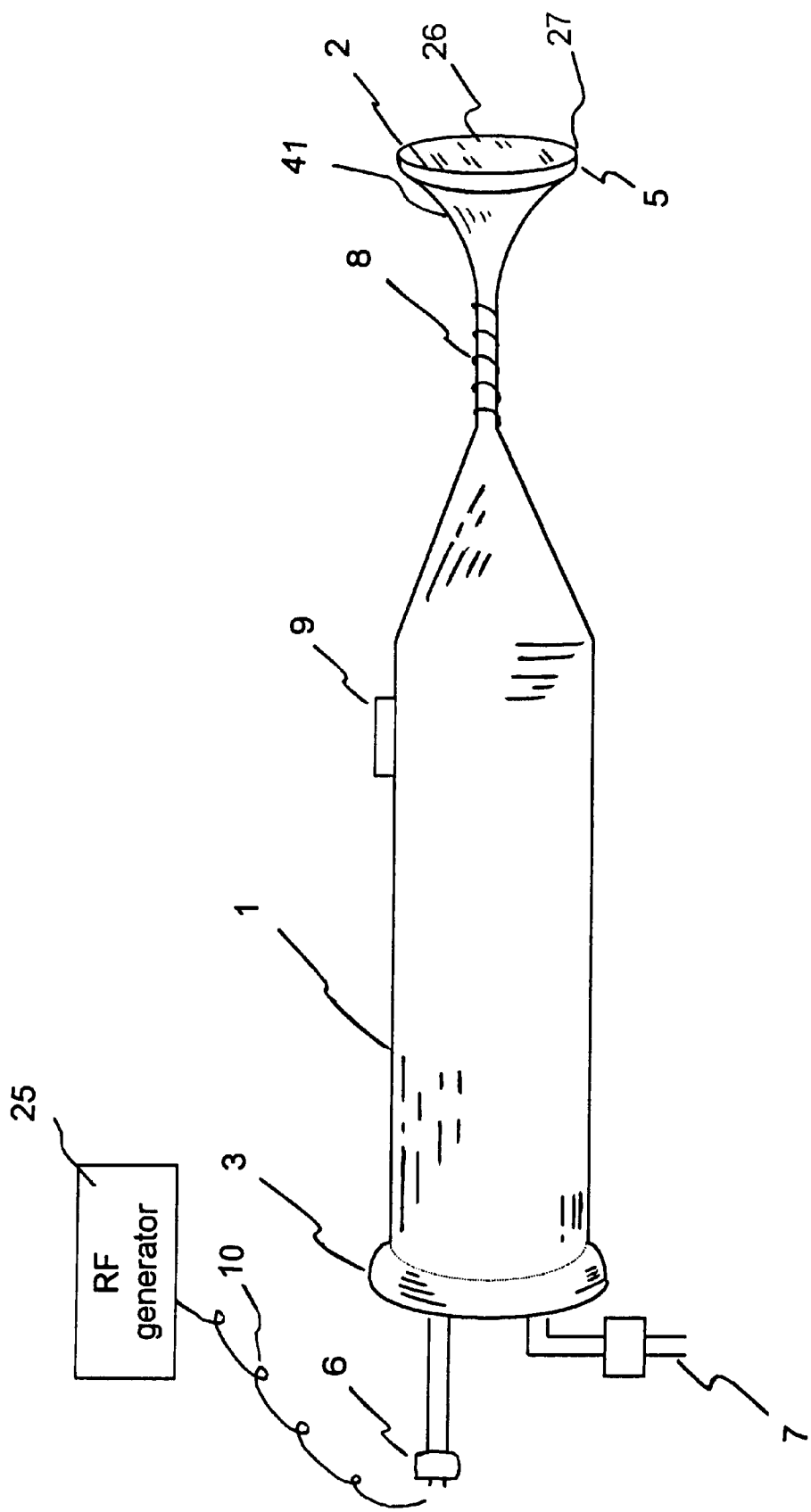
FIG. 1 is a perspective view of the device having rim electrode means for providing thermal energy to treat the tissues and fluid irrigation means for providing positive pressure to the medicament, constructed in accordance with the principles of the present invention.

Referring to FIGS. 1 to 7, what is shown is an embodiment of the device system by simultaneously applying radiofrequency energy and supplying a therapeutic fluid to treat the canker sores and other tissues of a patient. Suitable energy other than radiofrequency can also be used for the intended tissue treatments. As shown in FIG. 1, the device system in the form of a tubular element 1 comprises a distal end 2, a proximal end 3, and at least one lumen 4 extending therebetween; wherein rim electrode means 5 is disposed at said distal end 2, and wherein said electrode means has tissue-contact surface plate 26 for contacting the target tissue. The tissue-contact surface plate may be permeable to the medicament so that the therapeutic agent can evenly and diffusely permeate through said surface plate to the tissue. The tissue-contact surface plate 26 is so designed that the rim 27 of the rim electrode means 5 is slightly distal to said tissue-contact surface with reference to a longitudinal tubular axis. Said device system also comprises a connector 6 disposed at said proximal end 3 of the tubular element 1 and means for applying radiofrequency energy from an external RF generator 25 to said electrode means 5 of the device system through an electrical conductor 10. In another embodiment, a fluid infusion means 7, possibly equipped with a syringe or a pump, is provided for pressurizing the irrigation of a desired therapeutic agent, in either fluid phase or gel phase, to the canker sores site through the permeable surface plate portion 26 of the rim electrode means 5. The distal portion of the device may comprise a coil-like element 8 or a coil-supported neck so that the distal portion close to the distal end is manually bendable or deflectable. A RF energy switch button 9 is located at a convenient location on the tubular element 1 for a clinician to control the "on" and "off" actions of RF energy delivery. The radially outer surface 41 of said device, except the rim electrode means at its distal end, is not conductive. In another embodiment, the rim portion 27 of the rim electrode means may be non-conductive.

Figure 2:
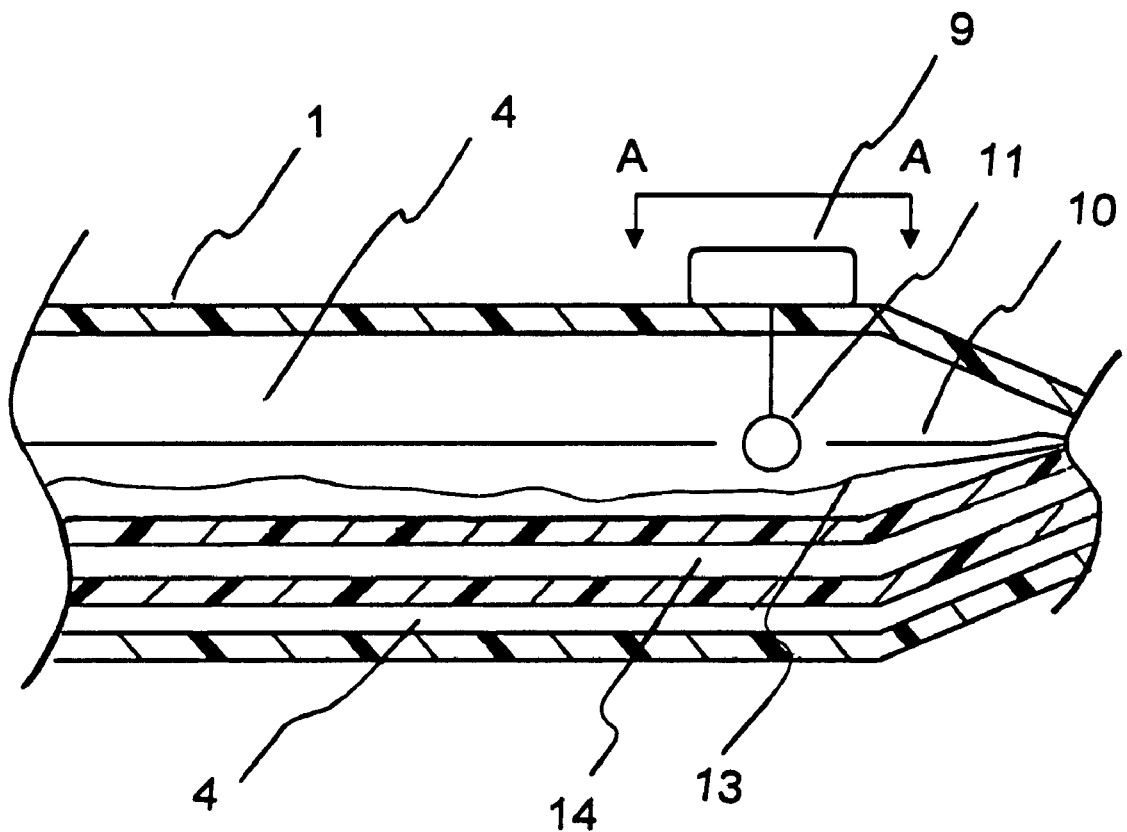
FIG. 2 is a cross-sectional view of the middle portion of the device in FIG. 1.

FIG. 2 is a cross-sectional view of the middle portion of the tubular element 1. At least one RF energy conducting wire 10 passes through the actuation mechanism 11 of the RF energy switch button 9 where the conducting wire is controlled "on" and "off" by a clinician. One end of said conducting wire 10 is secured and connected to the rim electrode means 5 at the distal end 2 while the other end of the conducting wire 10 is secured to a contact pin of the connector 6, wherefrom said conducting wire 10 is connected to an external RF generator 25 as shown in FIG. 1. The RF generator 25 may get its power 33 from AC or DC sources. The RF generator 25 may be equipped with a RF current splitter so that the RF current can be splitted through a plurality of energy conducting wires to each of the electrode means.

Figure 3:
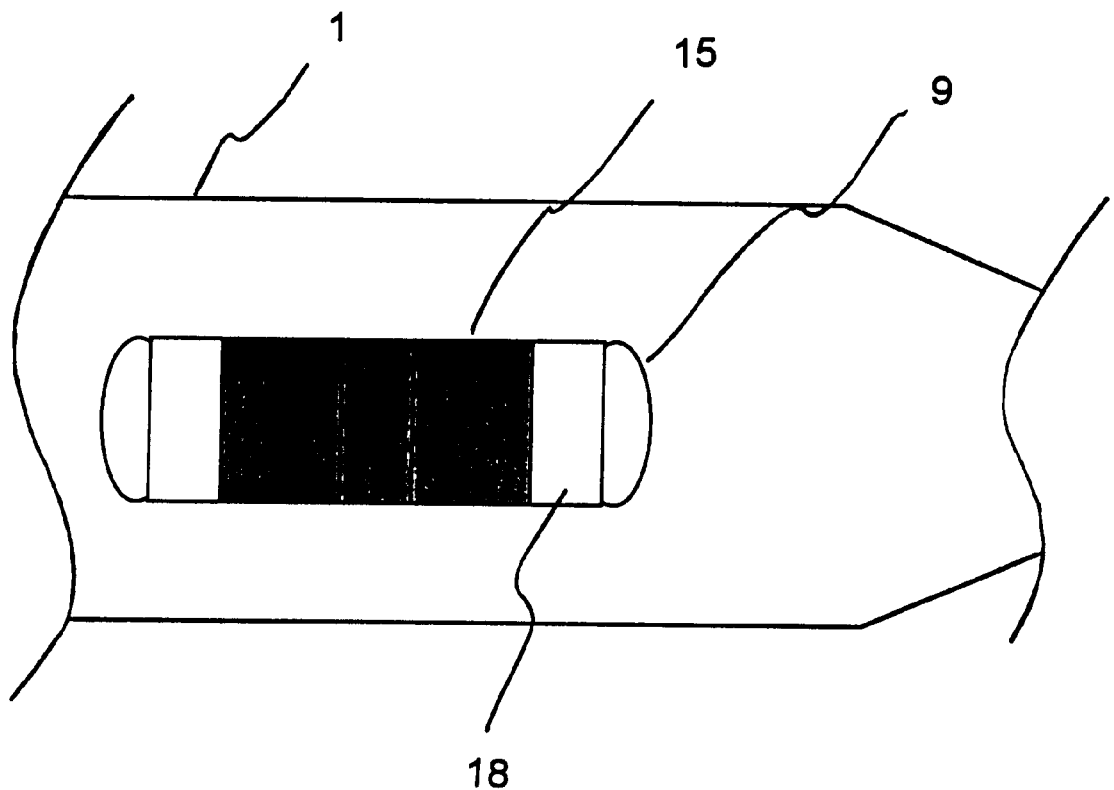
FIG. 3 is a top-view of the RF energy trigger button of FIG. 2; section A—A.

FIG. 3 is a top-view of the RF energy trigger button 9, section A—A of FIG. 2. It comprises at least one button 15, wherein this button controls one RF energy delivery means 10. In a multiple RF delivery system having a RF generator equipped with a current splitter, a plurality of buttons is provided for the system. Each button can individually be controlled for selected RF energy delivery to a specific electrode. In a preferred embodiment, a combination of different suitable energy sources can be applied to the device and controlled by a plurality of buttons. In another embodiment, the rim electrode means 5 at the distal end 2 comprises a main rim electrode as the outer rim and at least one other auxiliary rim electrode inside the rim of said main rim electrode. The rim portion 27 of the rim electrode means 5 is to provide a watertight system for the tubular element 1 so that the therapeutic fluid or gel can be infused and held for a prolonged duration when the rim electrode is pressed firmly against the tissue inside the mouth of a patient or at other appropriate location. The base frame 18 of the trigger button 9 is secured to an outer surface of the tubular element 1 at a convenient location for clinician's operation.

Figure 4:
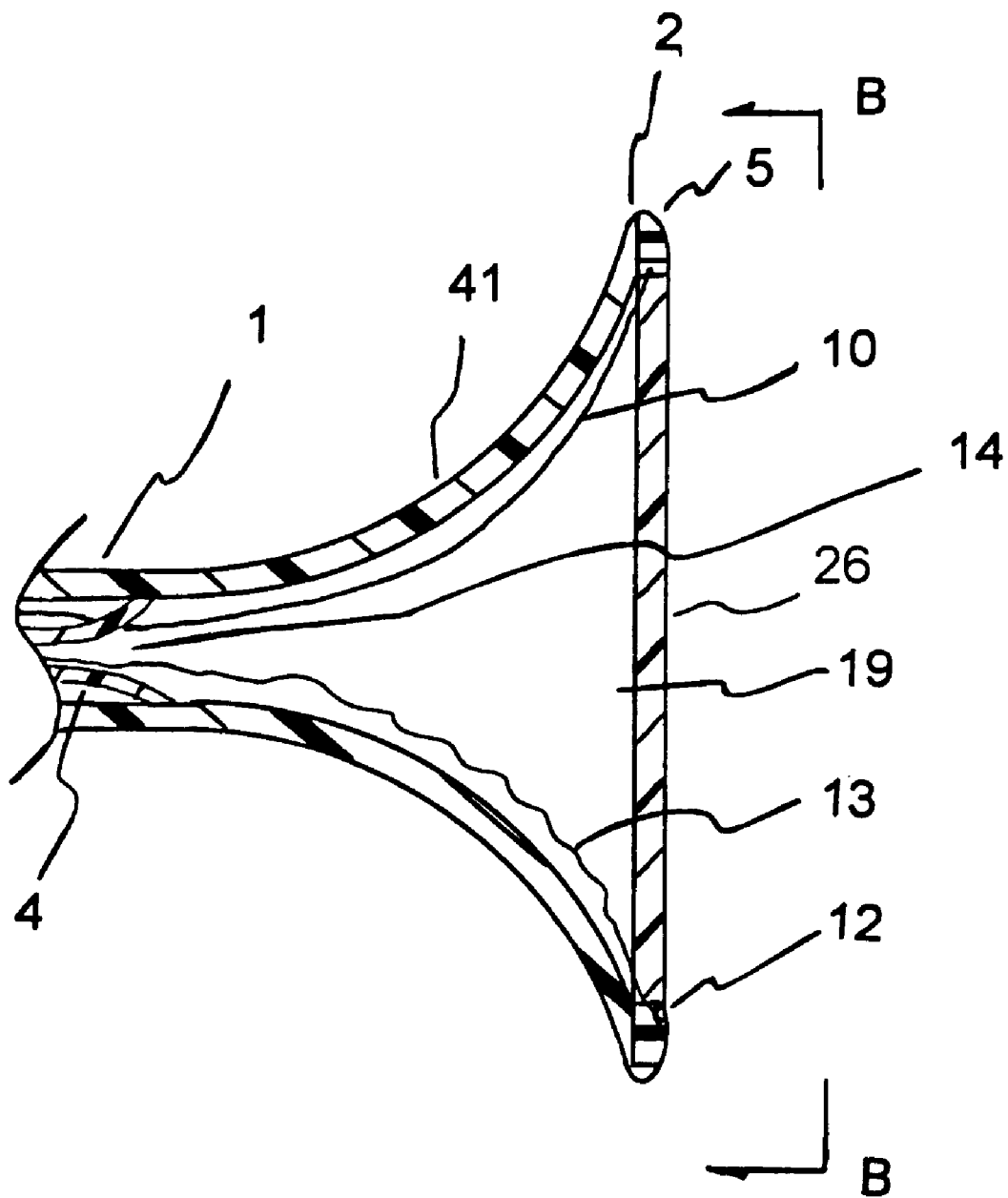
FIG. 4 is a side cross-sectional view of the distal portion of the device in FIG. 1.

FIG. 4 is a side cross-sectional view of the distal portion of the tubular element 1. The rim electrode means 5 is securely attached to the distal end 2 of the tubular element 1. A fluid conduit 14, located within the lumen 4 of the tubular element 1, is to provide the therapeutic fluid, preferably having a positive pressure by the fluid infusion means 32 to the irrigation port means 19 at the distal end 2 adjacent to the electrode means 5.

Temperature sensing means 12 is disposed close to or adjacent the rim electrode means 5. An insulated temperature sensor wire means 13 passes from the temperature sensing means 12 at the distal end, to an external temperature control mechanism 31 through the outlet connector 6. The RF energy delivery is controlled by a measured temperature and by a closed-loop temperature control mechanism 31 and/or algorithm. In one embodiment, fluid infusion means 32 is provided for irrigation of the therapeutic agent. The fluid infusion means may exert a positive pressure to transport the therapeutic from the proximal end to the distal end and to diffuse out of the permeable surface plate 26. Said therapeutic agent may be selected from the group consisting of heparin solution, saline solution, fluoroquinolone, lactic acid, glycolic acid, alpha hydroxy organic acids, vitamins, povidone-iodine, nitrate compounds, virucidal agents, anti-inflammatory agents, antibiotics, silver-containing fluid, and their mixtures. A conduit 14 is provided inside the lumen 4 for transporting said fluid or gel from the proximal end of a tubular element 1 to the distal end 2, wherein the fluid or gel has positive pressure exerted by fluid infusion means for infusing fluid/gel into the duct at proximity of the proximal end.

The rim electrode means 5 comprises a tissue-contact surface plate 26 at its distally outer surface plate, wherein the distally outer surface plate of said rim electrode means is permeable to medicament.

Figure 5:
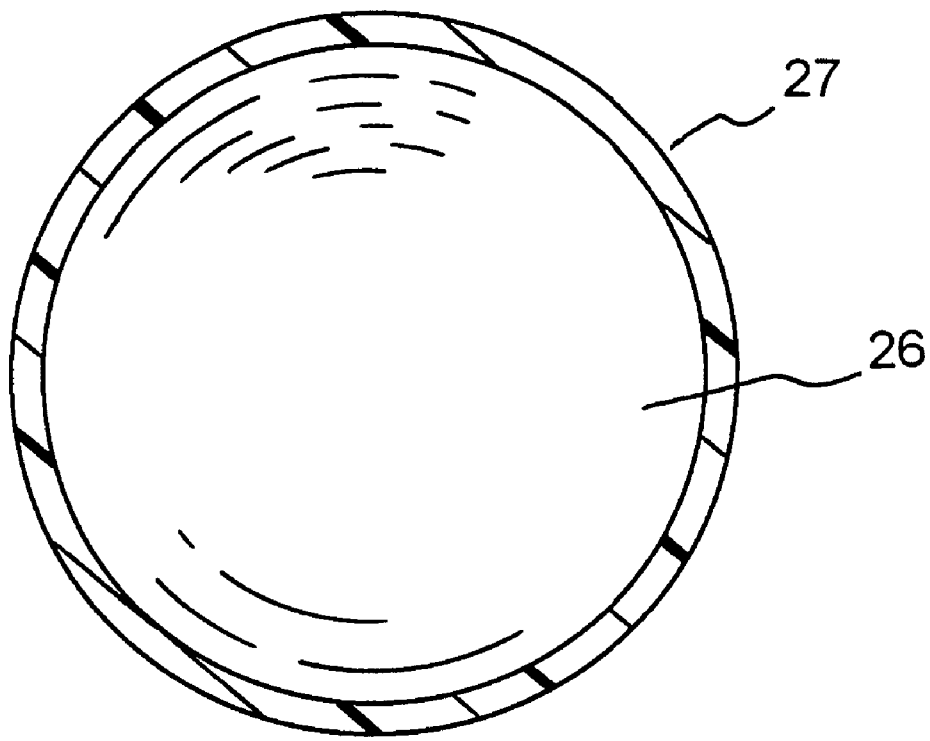
FIG. 5 is an end-view of the distal portion of the device of FIG. 4; section B—B, having a permeable tissue-contact surface plate.

FIG. 5 is an end-view of the distal portion of one type of the devices of the present invention; section B—B of FIG. 4. In this embodiment, the electrode means 5 of the device system comprises a rim 27 and a tissue-contact surface plate 26 which is also defined as the "distally outer surface plate" of the rim electrode means 5. The distally outer surface plate 26 is permeable to medicament, wherein the distally outer surface plate may be made of a conductive material so that RF energy can be applied through it to the underlying tissue 34 of the canker sore region 16. The distally outer surface plate 26 may be a separate component that is securable onto the rim electrode means 5 during use and exchangeable with a new surface plate 26. The RF current can also pass through the therapeutic agent to the tissue 34. In this case, the therapeutic agent contains electrolyte or ions for conducting the radiofrequency current to the tissue. The temperature of the therapeutic agent near the tissue contact region increases because the RF energy causes the tissue to heat-up. Said rim electrode means 5 is connected with a conducting wire 10, which passes through the trigger button 9 and terminates at the connector 6 of the proximal end 3 of the tubular element 1. In a further embodiment, there is at least one non-conductive zone on the tissue-contact distally outer surface plate 26. At least one irrigation port 19 is disposed at the distal end of said tubular element and becomes the reservoir for the permeable surface plate 26. By simultaneously applying RF energy to the rim electrode means and supplying the therapeutic fluid topically, the canker sores can be treated. During the RF ablation, therapeutic fluid, in liquid or gel form, is provided through the irrigation port 19 to the canker sore region, preferably under a positive pressure from the fluid irrigation means 32.

A method of applying a therapeutic agent to treat the canker sores of a patient comprises the steps of inserting a device into the mouth of a patient, wherein the device has a distal section, a distal end, a proximal end, openings at both ends, and at least one lumen extending therebetween, wherein rim electrode means is disposed at said distal end, and wherein said device is leak-proof except for the openings at the distal end and the proximal end. The method further comprises the steps of (a) contacting the device against the canker sores of a patient, wherein a distal surface plate of said rim electrode means covers the canker sore, and wherein said surface plate is permeable to medicament; (b) supplying a therapeutic agent to the canker sores, wherein a positive pressure is applied to said therapeutic agent from the proximal end of said device by fluid infusion means for pressurizing the therapeutic agent against the canker sores; (c) applying energy to the rim electrode means of the device, wherein the energy is selected from the group consisting of radiofrequency energy, microwave energy, ultrasonic energy, alternating current energy, and laser energy; and (d) maintaining contact of the therapeutic agent against the canker sores for a pre-determined time.

Figure 6:
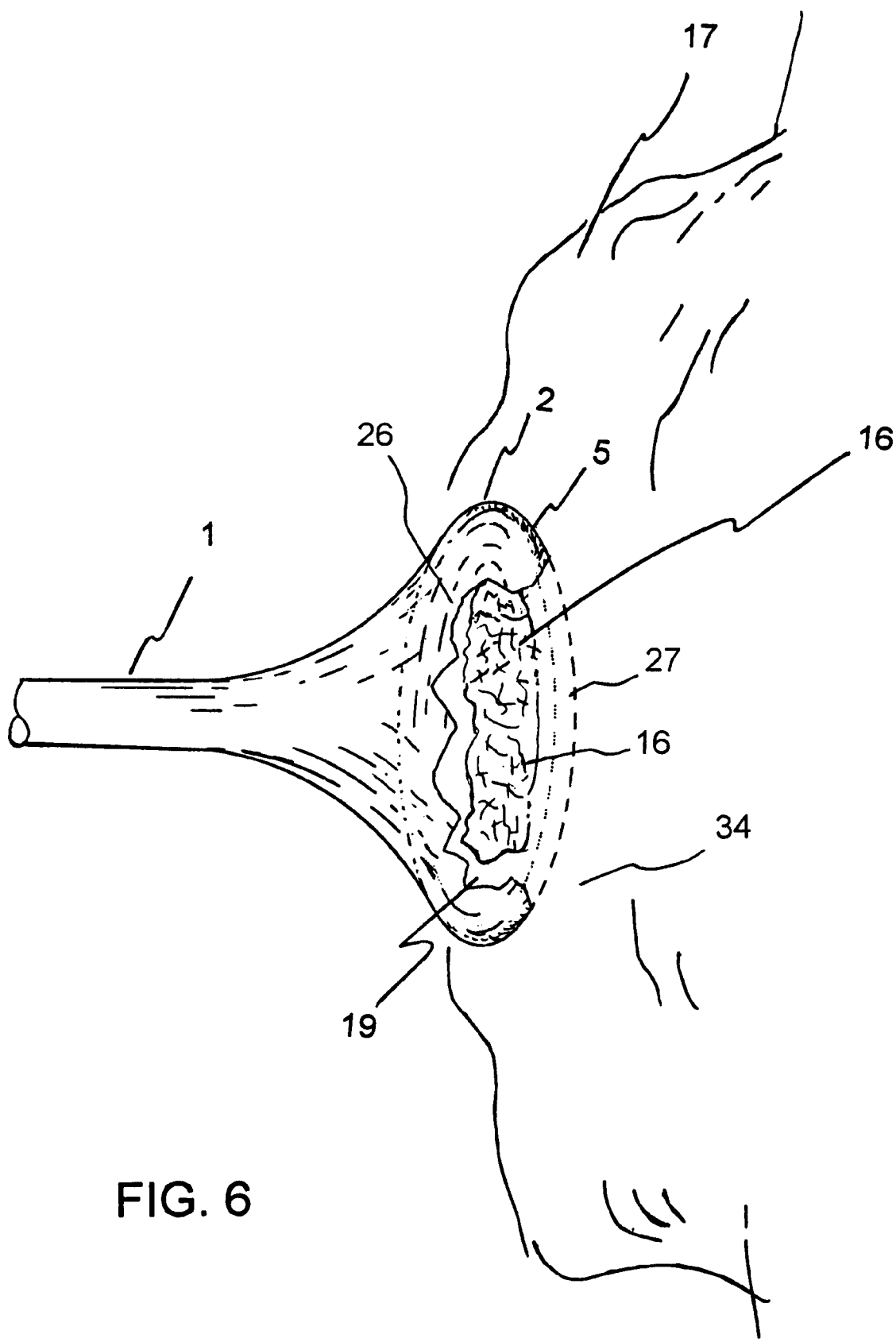
FIG. 6 shows a perspective view of a canker sore region being treated by the device and means of the present invention.

FIG. 6 shows a perspective view of a patient's mouth, wherein a canker sore region 16 is part of the mucus membrane 17 of the mouth tissue 34. The tubular element 1 of the present device system comprises a distal end 2, the rim electrode means 5, the rim 27, and a distally outer surface plate 26 to cover/contact the canker sore region 16. After firmly covering the canker sore region 16, the therapeutic fluid is infused and heated in-situ by suitable energy sources, such as radiofrequency energy, a miniature inserted heater, an ultrasound transducer and the like. The therapeutic fluid evenly and diffusely contacts the canker sore for a prolonged duration through the fluid-permeable tissue contact surface plate 26 until the symptom subsides. The RF energy generator 25 has the capability to supply RF energy by controlling the time, power and temperature, through a separately closed-loop temperature control means 31.

Figure 7:
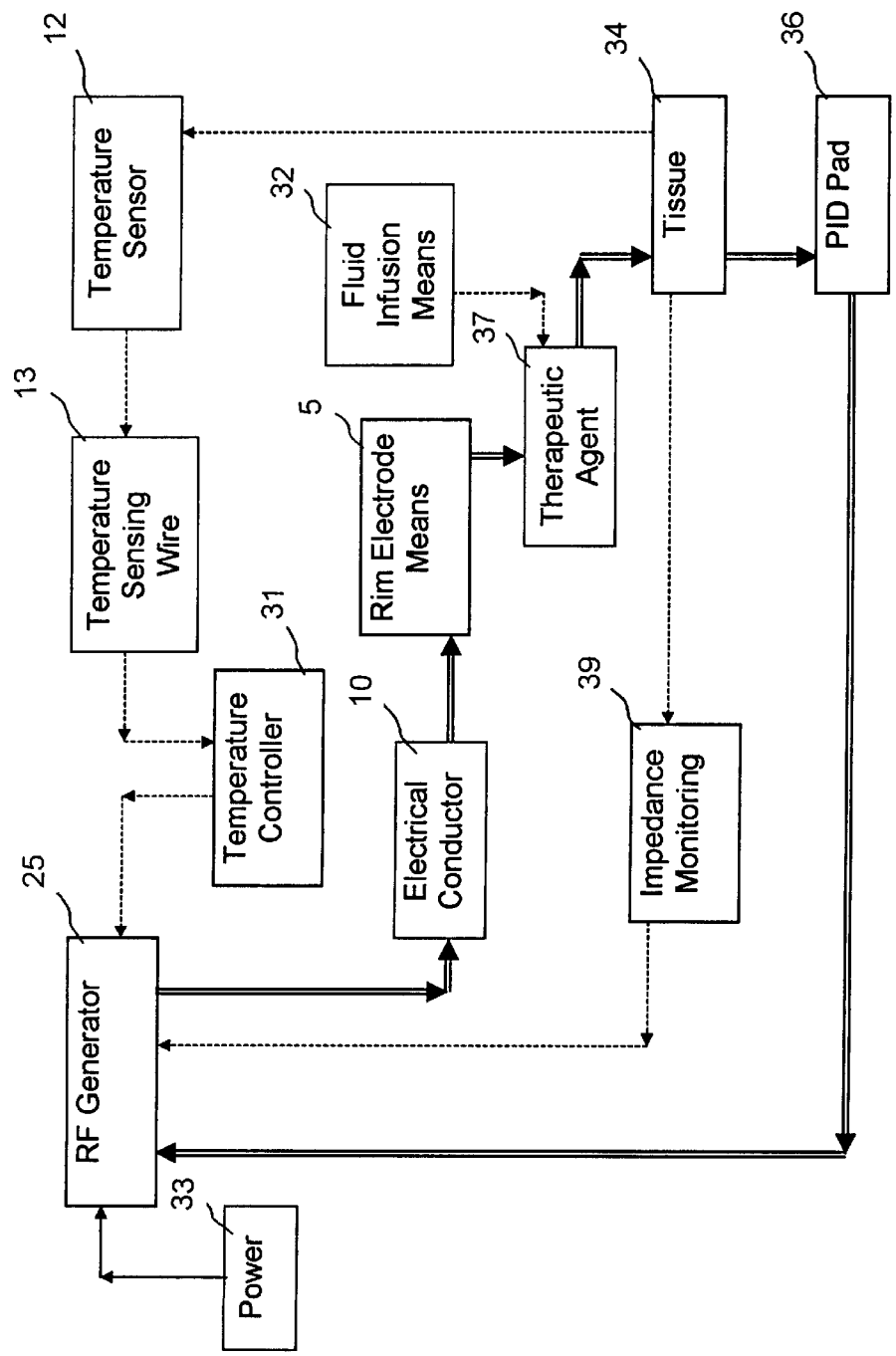
FIG. 7 is a schematic diagram of the RF delivery system.

FIG. 7 shows a schematic diagram of the RF delivery system. The patient is connected to the RF generator through a DIP electrode 36 to form a closed-loop current system. Therefore, radiofrequency energy is applied and delivered to the target canker sore region through the electrode means 5 and therapeutic agent 37 of this invention. The preferred radiofrequency energy current in this invention is within the range of 50 to 2,000 kHz. Impedance 39 measured from the tissue contact 34 is to ensure good tissue contact for ablation, otherwise the RF power is cutoff when the impedance is unreasonably high.

In a particular embodiment, the opening area of the distal end of the device for canker sore treatment is from 5 mm$^2$ to 100 mm$^2$ or larger. The tissue contacting electrode means 5 comprises at least one conducting surface zone or area. The material for the electrode means 5 of this invention may consist of conductive metals such as platinum, iridium, gold, silver, stainless steel, Nitinol, or an alloy of these metals.

From the foregoing description, it should now be appreciated that a medical device system for canker sores and other diseased tissues, comprising a suitable energy source and a therapeutic fluid irrigation capability has been disclosed. Several special features of the present invention make the device particularly suitable for treating the tissues.

The special features may include radiofrequency thermal therapy to the canker sores, positive pressure for fluid effusion, permeable tissue-contact surface plate, and heated therapeutic agent. While the invention has been described with reference to a specific embodiment, the description is illustrative of the invention and is not to be construed as limiting the invention. Various modifications and applications may occur to those who are skilled in the art without departing from the true spirit and scope of the invention as described by the appended claims.

What is claimed is:

1. A method of applying a therapeutic agent to treat the canker sores of a patient, the method comprising:
    (a) inserting a device into the mouth of a patient, wherein the device has a distal section, a distal end, a proximal end, openings at both ends, and at least one lumen extending therebetween, wherein rim electrode means is disposed at said distal end, and wherein said device is leak-proof except for the openings at the distal end and the proximal end;
    (b) contacting the device against the canker sores of a patient, wherein a distal surface plate of said rim electrode means covers the canker sore, and wherein said surface plate is permeable to medicament;
    (c) supplying a therapeutic agent to the canker sores, wherein a positive pressure is applied to said therapeutic agent from the proximal end of said device by fluid infusion means for pressurizing the therapeutic agent against the canker sores;
    (d) applying energy to the rim electrode means of the device, wherein the energy is selected from the group consisting of radiofrequency energy, microwave energy, ultrasonic energy, alternating current energy, and laser energy; and
    (e) maintaining contact of the therapeutic agent against the canker sores for a predetermined time.

2. A method of applying a therapeutic agent to treat the canker sores of a patient as in claim 1, wherein a rim portion of said rim electrode means is not electrically conductive.

3. A method of applying a therapeutic agent to treat the canker sores of a patient as in claim 1, further comprising a temperature sensor, wherein said temperature sensor is disposed at the distal surface plate of the rim electrode means.

4. A method of applying a therapeutic agent to treat the canker sores of a patient as in claim 3, further comprising a temperature controlling means, wherein a measured temperature of the temperature sensor is used as an input for the temperature controlling means to control the temperature.

5. A method of applying a therapeutic agent to treat the canker sores of a patient as in claim 1, further comprising the distal section having a radially outer surface plate, wherein the radially outer surface plate of said distal section is non-conductive.

6. A method of applying a therapeutic agent to treat the canker sores of a patient as in claim 1, wherein a surface of the distal surface plate of said rim electrode means is selected from the group consisting of a smooth surface, a rough surface, an irregular surface, a polished surface and a meshed surface.

7. A method of applying a therapeutic agent to treat the canker sores of a patient as in claim 2, wherein said therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, silver-containing fluid, and their mixtures.

8. A medical device for applying a therapeutic agent to treat the canker sores of a patient, comprising:
   (a) an elongated tubular element having a distal section, a distal end, a proximal end, openings at both ends, and at least one lumen extending therebetween, wherein rim electrode means having a distal surface plate is disposed at said distal end, and wherein said device is leak-proof except for the openings at the distal end and the proximal end;
   (b) the distal surface plate of said rim electrode means being permeable to medicament;
   (c) a handle secured at said proximal end of the tubular element;
   (d) means for supplying the therapeutic agent to the distal end of said device, wherein a positive pressure is applied to said therapeutic agent from the proximal end of said device by fluid infusion means for pressurizing the therapeutic agent against the canker sores;
   (e) means for heating the therapeutic agent in situ by energy of the rim electrode means, wherein the energy is selected from the group consisting of radiofrequency energy, microwave energy, ultrasonic energy, alternating current energy, and laser energy; and
   (e) means for applying energy to the rim electrode means of said device.

9. A medical device as in claim 8, wherein a rim portion of said rim electrode means is not electrically conductive.

10. A medical device as in claim 8 further comprising a temperature sensor, wherein said temperature sensor is disposed at the distal surface plate of the rim electrode means.

11. A medical device as in claim 10, further comprising temperature controlling means, wherein a measured temperature of said temperature sensor is used as an input for the temperature controlling means to control the temperature.

12. A medical device as in claim 8, wherein the radiofrequency energy current is within the range of 50 to 2,000 kHz.

13. A medical device as in claim 8, wherein said distal section of the device comprises a bendable section.

14. A medical device as in claim 8, further comprising the distal section with a radially outer surface plate, wherein the radially outer surface plate of said distal section is non-conductive.

15. A medical device as in claim 8, wherein said rim electrode means is constructed of a material selected from the group consisting of platinum, iridium, gold, silver, stainless steel, Nitinol, and an alloy of their mixture.

16. A medical device as in claim 8, wherein the therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, silver-containing fluid, and their mixtures.

17. A medical device as in claim 8, wherein the distal section of the rim electrode means is trumpet-shaped.

18. A device system for applying radiofrequency energy to treat a tissue, the device system comprising:
   (a) an elongated tubular element having a distal section, a distal end, a proximal end, openings at both ends, and at least one lumen extending therebetween, the electrode means disposed at said distal end, wherein said electrode means has at least one surface zone for contacting the tissue, wherein the at least one surface zone is permeable to medicament;
   (b) a handle secured at said proximal end of the tubular element;
   (c) means for supplying a therapeutic agent to the distal end of said device, wherein a positive pressure is applied to said therapeutic agent from the proximal end of said device by fluid infusion means for pressurizing the therapeutic agent against the canker sores; and
   (d) means for applying radiofrequency energy to the electrode means of said device for heating the therapeutic agent in situ, wherein radiofrequency energy is provided by a RF generator.

19. A device system as in claim 18, further comprising a temperature sensor, wherein said temperature sensor is disposed at the distal end of said device.

20. A device system as in claim 18, wherein the therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, silver-containing fluid, and their mixtures.

* * * * *